(12) United States Patent
Baker et al.

(10) Patent No.: US 11,587,656 B2
(45) Date of Patent: Feb. 21, 2023

(54) PERSONALIZED ASSISTANCE SYSTEM FOR USER OF VISION CORRECTION DEVICE

(71) Applicant: Alcon Inc., Fribourg (CH)

(72) Inventors: Kevin Baker, Duluth, GA (US); Ramesh Sarangapani, Coppell, TX (US)

(73) Assignee: Alcon Inc., Fribourg (CH)

(*) Notice: Subject to any disclaimer, the term of this patent is extended or adjusted under 35 U.S.C. 154(b) by 103 days.

(21) Appl. No.: 17/127,735

(22) Filed: Dec. 18, 2020

(65) Prior Publication Data

US 2021/0193278 A1 Jun. 24, 2021

Related U.S. Application Data

(60) Provisional application No. 62/950,432, filed on Dec. 19, 2019.

(51) Int. Cl.
*G16H 20/00* (2018.01)
*G16H 40/67* (2018.01)
(Continued)

(52) U.S. Cl.
CPC .............. *G16H 20/00* (2018.01); *A61B 3/04* (2013.01); *G06N 20/00* (2019.01); *G16H 10/20* (2018.01); *G16H 40/67* (2018.01); *G16H 80/00* (2018.01)

(58) Field of Classification Search
CPC ........ G16H 20/00; G16H 40/67; G16H 10/20; G16H 80/00; G16H 10/60; G16H 15/00; G16H 50/20; G16H 50/30; G06N 20/00; A61B 3/04; A61B 5/165; A61B 5/164; A61B 5/4088; A61B 5/4803; A61B 5/01; A61B 5/024; A61B 5/0816; A61B 5/11;
(Continued)

(56) References Cited

U.S. PATENT DOCUMENTS

2005/0160009 A1 7/2005 Tanaka et al.
2011/0084834 A1* 4/2011 Sabeta ................. G06K 19/077
340/540
(Continued)

FOREIGN PATENT DOCUMENTS

WO 2018199850 A1 11/2018
WO 2019175669 A1 9/2019
WO 2020261010 A1 12/2020

*Primary Examiner* — Hai Phan
*Assistant Examiner* — Anthony D Afrifa-Kyei

(57) ABSTRACT

A personalized assistance system for a user of a vision correction device includes a remote computing unit with a controller having a processor and tangible, non-transitory memory on which instructions are recorded. The controller is configured to selectively execute one or more machine learning models. A user device is operable by the user and includes an electronic diary module configured to prompt the user to answer one or more preselected questions at specific intervals. The electronic diary module is configured to store respective answers, entered by the user in response to the one or more preselected questions, as self-reported data. The controller is configured to obtain the self-reported data from the electronic diary module and generate an analysis of the self-reported data, via the one or more machine learning models. The controller is configured to assist the user based in part on the analysis.

17 Claims, 2 Drawing Sheets

(51) Int. Cl.
*G16H 10/20* (2018.01)
*G16H 80/00* (2018.01)
*G06N 20/00* (2019.01)
*A61B 3/04* (2006.01)

(58) Field of Classification Search
CPC .. A61B 5/14551; A61B 5/7275; G09B 19/00;
G10L 25/66; G10L 15/00; G10L 21/00;
G10L 15/18; G10L 15/183; G10L 25/00;
G10L 25/48; G10L 25/51; G06F 16/24
See application file for complete search history.

(56) References Cited

U.S. PATENT DOCUMENTS

| | | |
|---|---|---|
| 2015/0100342 A1 | 4/2015 | Schulte |
| 2017/0092235 A1* | 3/2017 | Osman .................. G06F 3/16 |
| 2017/0340200 A1* | 11/2017 | Blaha .................. A61B 3/113 |
| 2018/0317766 A1* | 11/2018 | Predham .............. A61B 3/111 |
| 2019/0029516 A1* | 1/2019 | Fried .................. A61B 3/0285 |
| 2020/0143701 A1* | 5/2020 | Letzt .................. G16H 40/67 |

\* cited by examiner

PERSONALIZED ASSISTANCE SYSTEM FOR USER OF VISION CORRECTION DEVICE

INTRODUCTION

The disclosure relates generally to a personalized assistance system for a user of a vision correction device and method. Humans have five basic senses: sight, hearing, smell, taste and touch. Sight gives us the ability to visualize the world around us and connects us to our surroundings. According to some scientific reports, the brain devotes more space to processing and storing visual information than the other four senses combined, underscoring the importance of sight. Many people worldwide have various issues with quality of vision, for example, due to refractive errors. At least some of these issues may be addressed with vision correction devices, such as spectacles and contact lenses.

SUMMARY

Disclosed herein is a personalized assistance system for a user of a vision correction device and method. The personalized assistance system includes a remote computing unit with a controller having a processor and tangible, non-transitory memory on which instructions are recorded. The controller is configured to selectively execute one or more machine learning models. A user device is operable by the user and configured to communicate with the remote computing unit. The user device includes an electronic diary module configured to prompt the user to answer one or more preselected questions at specific intervals.

The electronic diary module is configured to store respective answers entered by the user in response to the one or more preselected questions as self-reported data. The one or more preselected questions may include an inquiry into a comfort level of the user, including at least one of a dryness factor and an irritation factor. The one or more preselected questions may include an inquiry into when the user last cleaned the vision correction device.

The controller is configured to obtain the self-reported data from the electronic diary module and generate an analysis of the self-reported data, via the one or more machine learning models. The controller is configured to assist the user based in part on the analysis. The vision correction device may include, but is not limited to, a contact lens. For example, the contact lens may be a multi-focal lens having a first zone for distance vision, a second zone for near vision and a third zone for intermediate vision.

The remote computing unit may include a first cloud unit and a central server, with the controller being embedded in at least one of the first cloud unit and the central server. The user device may include a query module configured to receive at least one question generated by the user. The controller may be configured to receive the question from the query module, formulate a reply, based in part on a first one of the one or more machine learning models, and post the reply, via the query module, for consumption by the user.

A provider device is configured to communicate with the remote computing unit, the provider device being operable by an eye care provider associated with the user. The user device and the provider device include respective message modules. The remote computing unit may be configured to provide two-way communication between the eye care provider and the user via the respective message modules.

The remote computing unit may include a first database storing respective information pertaining to the user, including a type of the vision correction device. The remote computing unit may include a second database storing group data pertaining to a group of users, the group data including respective self-reported data of the group of users. The user device includes a comparative tracking module configured to enable the user to compare the self-reported data with the group data. Assisting the user may include at least one of: providing coaching on taking care of the vision correction device and/or an eye of the user; suggesting a follow-up visit with an eye care provider; and suggesting an alternative vision correction product.

The above features and advantages and other features and advantages of the present disclosure are readily apparent from the following detailed description of the best modes for carrying out the disclosure when taken in connection with the accompanying drawings.

DETAILED DESCRIPTION

Figure 1:
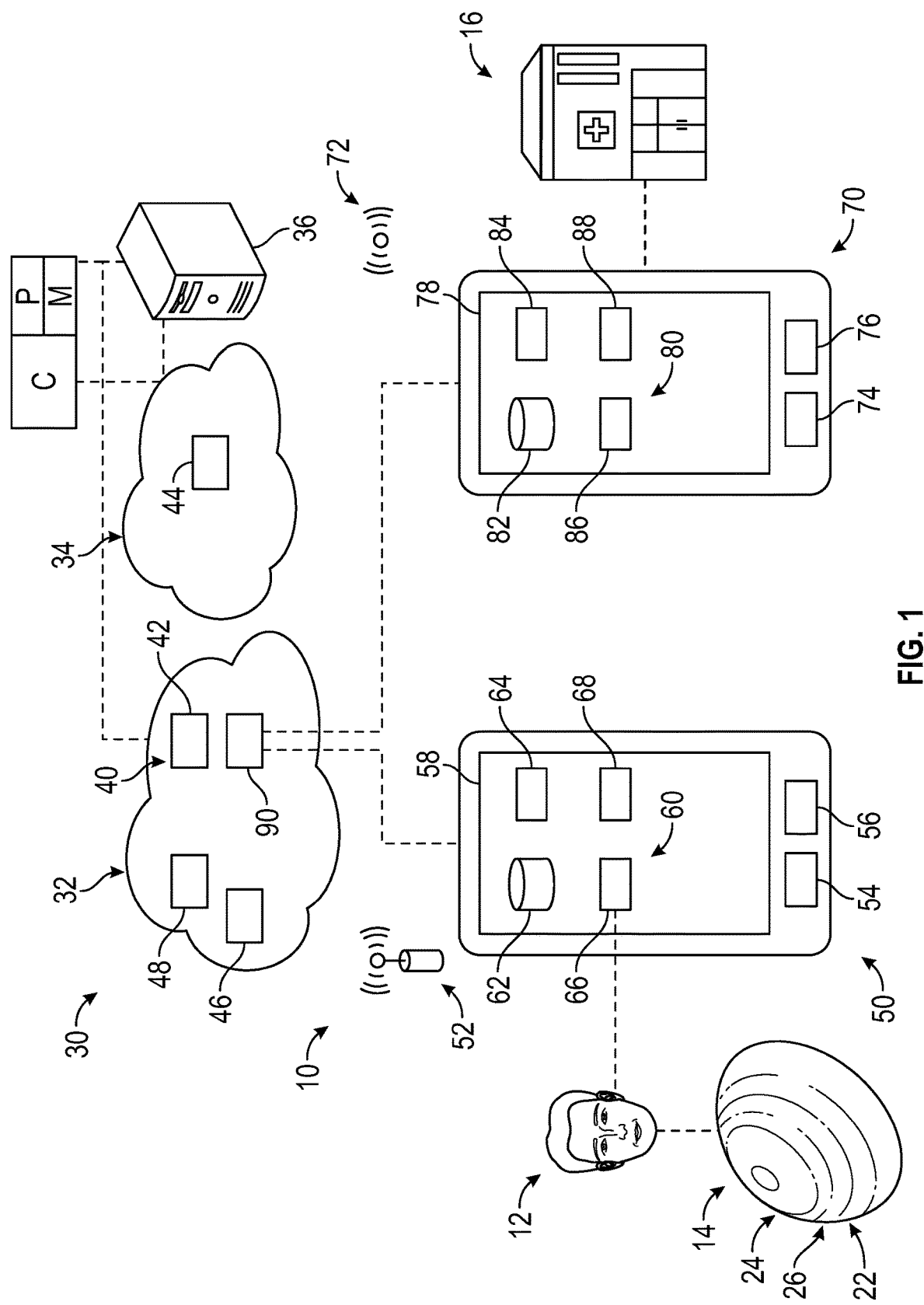
FIG. 1 is a schematic illustration of a personalized assistance system having a remote computing unit with a controller.

Referring to the drawings, wherein like reference numbers refer to like components, FIG. 1 schematically illustrates a personalized assistance system 10 for assisting a user 12 of a vision correction device 14. The personalized assistance system 10 may include interfacing the user 12 with an eye care provider 16 associated with the user 12. The personalized assistance system 10 is configured to address problems leading to a user 12 no longer wearing the vision correction device 14, i.e. mitigate a drop-off in the use of the vision correction device 14 by the user 12. In one example, the vision correction device 14 is a contact lens having multiple zones with different respective optical powers, such as a first zone 22 for distance vision, a second zone 24 for near vision and an third zone 26 for intermediate vision. It is to be understood that the contact lens may take many different forms and include multiple and/or alternate components. Additionally, any type of vision correction device available to those skilled in the art may be employed.

The user 12 may employ the personalized assistance system 10 after being fitted with the vision correction device 14 by the eye care provider 16 to achieve a number of goals, including but not limited to: reporting outcomes over time so that progress can be tracked and monitored, asking questions and getting answers in real-time, and receiving personalized suggestions based on past reported outcomes and past queries. Additionally, the personalized assistance system 10 may be configured to respond to specific actions requested by the user 12. For example, a user 12 may request setting up of a reminder to remove their vision correction device 14. As described below, the personalized assistance system 10 leverages both self-reported data and comparative data for optimizing the experience of the user 12.

Referring to FIG. 1, the personalized assistance system 10 includes a remote computing unit 30 having a controller C. The controller C has at least one processor P and at least one memory M (or non-transitory, tangible computer readable storage medium) on which are recorded instructions for executing a method 100. Method 100 is shown in and described below with reference to FIG. 2.

Referring to FIG. 1, the remote computing unit 30 may include one or cloud units, such as a first cloud unit 32, a second cloud unit 34 and a central server 36. The controller C may be embedded in at least one of the cloud units and the central server 36. The central server 36 may be a private or public source of information maintained by an organization, such as for example, a research institute, a company, a university and/or a hospital. The first cloud unit 32 and the second cloud unit 34 may include one or more servers hosted on the Internet to store, manage, and process data.

The controller C has access to and is specifically programmed to selectively execute one or more machine learning models 40, such as first machine learning model 42 and second machine learning model 44. The machine learning models 40 may be configured to find parameters, weights or a structure that minimizes a respective cost function. Each of the machine learning models 40 may be a respective regression model. In one example, the first machine learning model 42 and the second machine learning model 44 are respectively embedded in the first cloud unit 32 and the second cloud unit 34. The remote computing unit 30 may include a first database 46 for storing respective information pertaining to the user 12, including the type of the vision correction device. The remote computing unit 30 may include a second database 48 for storing group data pertaining to a group of users.

Referring to FIG. 1, a user device 50 is operable by the user 12 and configured to communicate with, i.e. receive and transmit wireless communication, the remote computing unit 30, via a first network 52. The user device 50 may include a respective processor 54 and a respective memory 56. The user device 50 may run a first application 58, which may be a mobile application or "app." The circuitry and components of a server, network and mobile application ("apps") available to those skilled in the art may be employed.

The user device 50 may be a smartphone, laptop, tablet, desktop or other electronic device that the user 12 may operate, for example with a touch screen interface or I/O device such as a keyboard or mouse. The plurality of modules 60 may be executed in coordination with the remote computing unit 30. In one example, the plurality of modules 60 includes an electronic diary module 62, a query module 64, a first messaging module 66 and a suggestion module 68. The plurality of modules 60 may consume the output of a common or different machine learning models 40.

The electronic diary module 62 is configured to prompt the user 12 to answer one or more preselected questions at specific intervals, e.g. daily. The electronic diary module 62 is configured to store respective answers entered by the user 12 in response to the one or more preselected questions as self-reported data. The one or more preselected questions may include an inquiry into a comfort level of the user 12, including at least one of a dryness factor and an irritation factor. The one or more preselected questions may include an inquiry into when the user 12 last cleaned the vision correction device 14. The controller C may be configured to obtain the self-reported data from the electronic diary module 62 and generate an analysis of the self-reported data, via the one or more machine learning models 40. The user 12 may compare the self-reported data with group data (second database 48) generated by other users of the same type of vision correction device 14, via the electronic diary module 62.

The controller C may be configured to assist the user 12 based in part on the analysis. Assisting the user 12 based in part on the analysis may include at least one of the following: providing coaching on taking care of the vision correction device 14 (e.g. cleaning procedures) and/or an eye of the user 12; comparing comfort scores and other markers at a specific time period (e.g. one week after being fitted with the vision correction device 14) for the user 12 relative to a group of users of the same product; suggesting a follow-up visit with the eye care provider 16; and suggesting an alternative vision correction product.

Referring to FIG. 1, the query module 64 in the user device 50 may be configured to receive at least one question entered by the user 12. The controller C may be configured to receive the at least one question from the query module 64 and formulate a reply, based in part on the one or more machine learning models 40. The reply may be posted, via the query module 64, for consumption by the user 12. The personalized assistance system 10 may be configured to be "adaptive" and may be updated periodically after the collection of additional data. In other words, the machine learning models 40 may be configured to be "adaptive machine learning" algorithms that are not static and that improve after additional user data is collected.

Referring to FIG. 1, a provider device 70 is operable by the eye care provider 16 associated with the user. The provider device 70 is configured to communicate with the remote computing unit 30 via a second network 72. The provider device 70 includes a respective processor 74 and a respective memory 76. Similar to the user device 50, the provider device 70 may run a second application 78 (incorporating a plurality of modules 80) that is executed in coordination with the remote computing unit 30. The plurality of modules 80 may include a patient database 82 (stratified by the type of vision correction device 14), a user progress tracker module 84 configured to track progress of the user 12 and other users associated with the eye care provider 16, a second message module 86 and a comparative tracking module 88 configured to provide trend and comparative analyses.

The remote computing unit 30 may be configured to provide two-way communication between the eye care provider 16 and the user 12 via the first message module 66 and the second message modules 86. Referring to FIG. 1, the personalized assistance system 10 may include a broker module 90 for routing the respective messages from the user 12 to the eye care provider 16, and vice-versa. The broker module 90 may be configured in different ways. While FIG. 1 shows an example implementation of the personalized assistance system 10, it is understood that other implementations may be carried out.

Referring to FIG. 1, the first network 52 and second network 72 may be wireless or may include physical components and may be a short-range network or a long-range network. For example, the first network 52 and second network 72 may be implemented in the form of a local area network. The local area network may include, but is not limited to, a Controller Area Network (CAN), a Controller Area Network with Flexible Data Rate (CAN-FD), Ethernet, blue tooth, WIFI and other forms of data connection. The local area network may be a Bluetooth™ connection, defined as being a short-range radio technology (or wireless technology) aimed at simplifying communications among Internet devices and between devices and the Internet. Bluetooth™ is an open wireless technology standard for transmitting fixed and mobile electronic device data over short distances and creates personal networks operating within the 2.4 GHz band. The local area network may be a Wireless Local Area Network (LAN) which links multiple devices using a wireless distribution method, a Wireless Metropolitan Area Networks (MAN) which connects several wireless LANs or a Wireless Wide Area Network (WAN) which covers large areas such as neighboring towns and cities. Other types of connections may be employed.

The machine learning models 40 of FIG. 1 may include a neural network algorithm. While a neural network is illustrated herein, it is understood that the machine learning models 40 may be based on different kinds or types of algorithms, including but not limited to, a neural network, support vector regression, linear or logistic regression, k-means clustering, random forest and other types. As understood by those skilled in the art, neural networks are designed to recognize patterns from real-world data (e.g. images, sound, text, time series and others), translate or convert them into numerical form and embed in vectors or matrices. The neural network may employ deep learning maps to match an input vector x to an output vector y. Stated differently, each of the plurality of machine learning models 40 learns an activation function $f$ such that $f(x)$ maps to y. The training process enables the neural network to correlate the appropriate activation function $f(x)$ for transforming the input vector x to the output vector y. In the case of a simple linear regression model, two parameters are learned: a bias and a slope. The bias is the level of the output vector y when the input vector x is 0 and the slope is the rate of predicted increase or decrease in the output vector y for each unit increase in the input vector x. Once the plurality of machine learning models 40 is respectively trained, estimated values of the output vector y may be computed with given new values of the input vector x.

Figure 3:
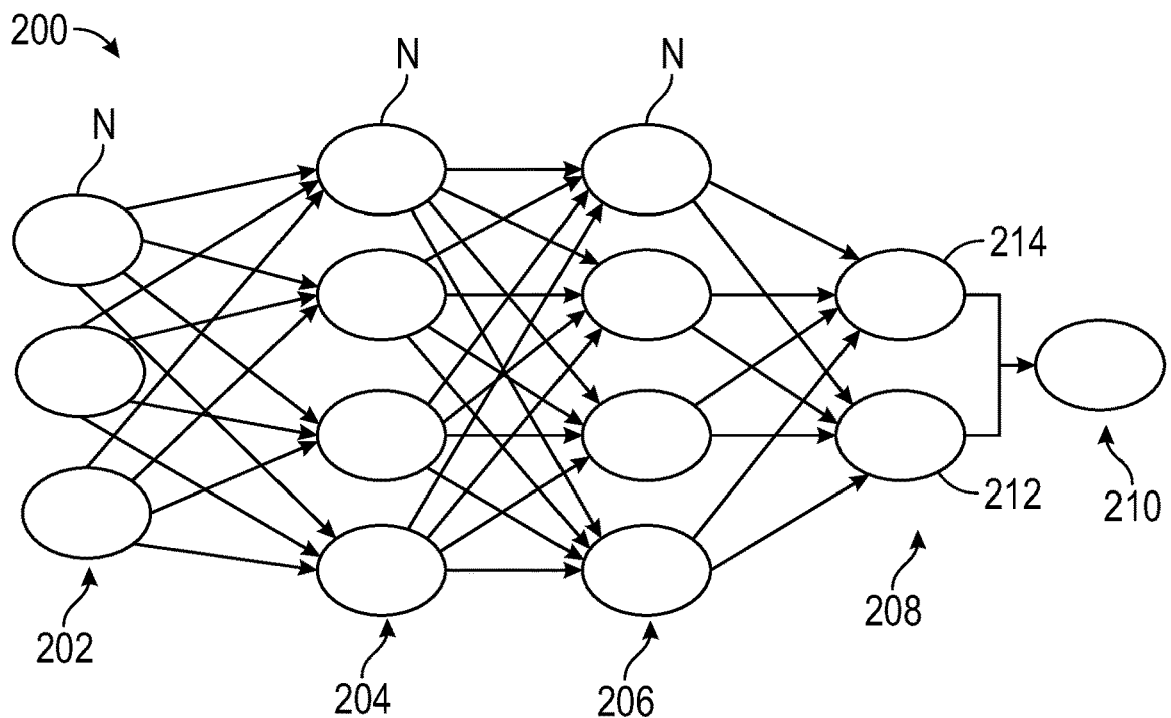
FIG. 3 is a schematic example of a machine learning model executable by the controller of FIG. 1.

Referring to FIG. 3, an example network 200 for the machine learning models 40 of FIG. 1 is shown. The example network 200 is a feedforward artificial neural network having at least three layers of nodes N, including an input layer 202, one or more hidden layers, such as first hidden layer 204 and second hidden layer 206, and an output layer 208. Each of the layers is composed of nodes N configured to perform an affine transformation of a linear sum of inputs. The nodes N are neurons characterized by a respective bias and respective weighted links. The nodes N in the input layer 202 receive the input, normalize them and forward them to nodes N in the first hidden layer 204. Each node N in a subsequent layer computes a linear combination of the outputs of the previous layer. A network with three layers would form an activation function $f(x)=f(3)(f(2)(f(1)(x)))$. The activation function $f$ may be linear for the respective nodes N in the output layer 210. The activation function $f$ may be a sigmoid for the first hidden layer 204 and the second hidden layer 206. A linear combination of sigmoids is used to approximate a continuous function characterizing the output vector y.

The example network 200 may generate multiple outputs, such as a first output factor 212 and a second output factor 214, with the controller C being configured to use a weighted average of the multiple outputs to obtain a final output 210. For example, if the inputs to the input layer 202 are various factors (e.g. comfort level, visual acuity score) pertaining to a particular type of vision correction device 14, the first output factor 212 and the second output factor 214 may be an objective satisfaction score and a subjective satisfaction score, respectively, for that particular type of vision correction device 14. Other machine learning models available to those skilled in the art may be employed.

Figure 2:
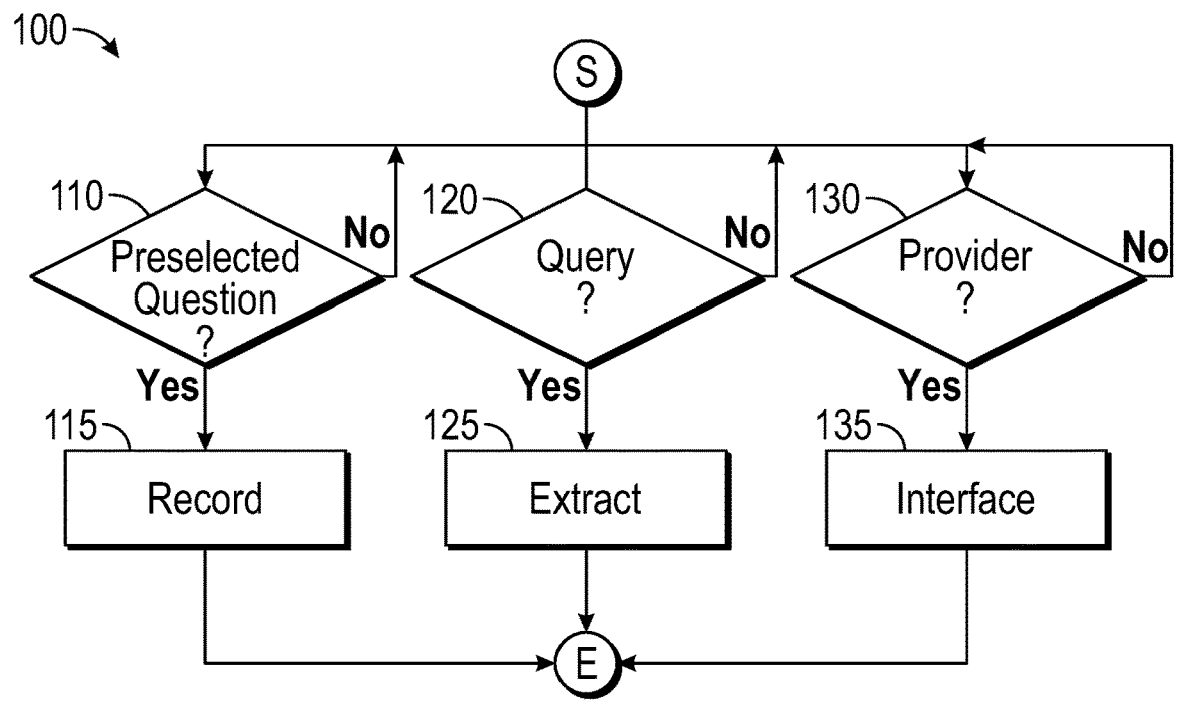
FIG. 2 is a schematic flowchart for a method executable by the controller of FIG. 1.

Referring now to FIG. 2, a flow chart of method 100 executable by the controller C of FIG. 1 is shown. Method 100 need not be applied in the specific order recited herein, with the start and end indicated respectively by "S" and "E" in FIG. 2. It is understood that some blocks may be omitted. The memory M can store controller-executable instruction sets, and the processor P can execute the controller-executable instruction sets stored in the memory M.

Per block 110 of FIG. 2, the controller C is configured to determine if the electronic diary module 62 has been triggered and the user 12 has answered any of the preselected questions. If so, the method 100 proceeds to block 115, where the controller C is configured to record the respective answers entered by the user 12. If not, the method 100 loops back to the start S.

Per block 120 of FIG. 2, the controller C is configured to determine if the query module 64 has been triggered and the user 12 has asked a question. If so, per block 125, the controller C is configured to formulate a reply, based in part on the one or more machine learning models 40 and post the reply, via the query module 64, for consumption by the user 12. For example, the controller C may extract keywords from the question and enter them as inputs into the input layer 202. The reply may be extracted based on the output layer 208 of the example network 200. If not, the method 100 loops back to the start S.

Per block 130 of FIG. 2, the controller C is configured to determine if one or more enabling conditions has been met. The enabling conditions may include an irritation factor and/or discomfort factor being above a predetermined threshold. If so, per block 135, the controller C may execute one or more actions, which may include interfacing with the eye care provider 16 via a message sent to the second message module 86. The actions may include posting a reminder via the suggestion module 68 in the user device 50, such as "please remember to clean contact lenses daily."

In summary, the personalized assistance system 10 employs a multi-prong approach utilizing one or more machine learning models 40. The personalized assistance system 10 may be configured to recognize non-adherence to suggested guidelines, recognize when a follow up visit to the eye care provider 16 makes sense or suggest an alternative contact lens. The personalized assistance system 10 offers an effective two-way communication between the user 12 and the eye care provider 16.

The controller C of FIG. 1 includes a computer-readable medium (also referred to as a processor-readable medium), including a non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random-access memory (DRAM), which may constitute a main memory. Such instructions may be transmitted by one or more transmission media, including coaxial cables, copper wire and fiber optics, including the wires that comprise a system bus coupled to a processor of a computer. Some forms of computer-readable media include, for example, a floppy disk, a flexible disk, hard disk, magnetic tape, other magnetic medium, a CD-ROM, DVD, other optical medium, punch cards, paper tape, other physical medium with patterns of holes, a RAM, a PROM, an EPROM, a FLASH-EEPROM, other memory chip or cartridge, or other medium from which a computer can read.

Look-up tables, databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store may be included within a computing device employing a computer operating system such as one of those mentioned above and may be accessed via a network in one or more of a variety of manners. A file system may be accessible from a computer operating system and may include files stored in various formats. An RDBMS may employ the Structured Query Language (SQL) in addition to a language for creating, storing, editing, and executing stored procedures, such as the PL/SQL language mentioned above.

The detailed description and the drawings or FIGS. are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A personalized assistance system for a user of a vision correction device, the personalized assistance system comprising:
   a remote computing unit including a controller having a processor and tangible, non-transitory memory on which instructions are recorded, the controller being configured to selectively execute one or more machine learning models, wherein the controller is configured to:
   adaptively train the one or more machine learning models based on a set of past data relating to a collection of past self-reported data, a collection of answers to one or more preselected questions asked at specific intervals, a collection of past questions received, and a collection of past replies;
   a user device operable by the user and configured to communicate with the remote computing unit, wherein the user device includes a query module configured to receive at least one question generated by the user;
   wherein the user device includes an electronic diary module configured to prompt the user to answer one or more preselected questions at specific intervals;
   wherein the electronic diary module is configured to store respective answers, entered by the user in response to the one or more preselected questions, as self-reported data;
   wherein the controller is configured to:
   obtain the self-reported data from the electronic diary module;
   receive the at least one question from the query module;
   generate an analysis of the self-reported data, via the one or more machine learning models; and
   assist the user based in part on the analysis by formulating a reply to the at least one question, based in part on the one or more machine learning models; and
   post the reply, via the query module, for consumption by the user.

2. The personalized assistance system of claim 1, wherein:
   the remote computing unit includes a first cloud unit and a central server, the controller being embedded in at least one of the first cloud unit and the central server.

3. The personalized assistance system of claim 1, further comprising:
   a provider device configured to communicate with the remote computing unit, the provider device being operable by an eye care provider associated with the user;
   wherein the user device and the provider device include respective message modules; and
   wherein the remote computing unit is configured to provide two-way communication between the eye care provider and the user via the respective message modules.

4. The personalized assistance system of claim 1, wherein:
   the remote computing unit includes a first database storing respective information pertaining to the user, including a type of the vision correction device;
   the remote computing unit includes a second database storing group data pertaining to a group of users, the group data at least partially including respective self-reported data of the group of users; and
   the user device includes a comparative tracking module configured to enable the user to compare the self-reported data with the group data.

5. The personalized assistance system of claim 1, wherein assisting the user based in part on the analysis includes at least one of:
   providing coaching on taking care of at least one of the vision correction device and an eye of the user;
   suggesting a follow-up visit with an eye care provider; and
   suggesting an alternative vision correction product.

6. The personalized assistance system of claim 1, wherein:
   the vision correction device is a contact lens.

7. The personalized assistance system of claim 6, wherein:
   the contact lens is a multi-focal lens having a first zone for distance vision, a second zone for near vision and a third zone for intermediate vision.

8. The personalized assistance system of claim 7, wherein the one or more preselected questions include:
   an inquiry into a comfort level of the user, including at least one of a dryness factor and an irritation factor.

9. The personalized assistance system of claim 7, wherein the one or more preselected questions include:
   an inquiry into when the user last cleaned the vision correction device.

10. A personalized assistance system for selectively interfacing a user of a vision correction device with an eye care provider associated with the user, the personalized assistance system comprising:
    a remote computing unit including a controller having a processor and tangible, non-transitory memory on which instructions are recorded, the controller being configured to:

selectively execute one or more machine learning models;

adaptively train the one or more machine learning models based on a set of past data relating to a collection of past self-reported data, a collection of answers to one or more preselected questions asked at specific intervals, a collection of past questions received, and a collection of past replies;

a user device operable by the user and configured to communicate with the remote computing unit, wherein the user device includes a query module configured to receive at least one question generated by the user;

a provider device configured to communicate with the remote computing unit, the provider device being operable by the eye care provider;

wherein the user device includes an electronic diary module configured to prompt the user to answer one or more preselected questions at specific intervals;

wherein the electronic diary module is configured to store respective answers, entered by the user in response to the one or more preselected questions, as self-reported data;

wherein the controller is configured to obtain the self-reported data from the electronic diary module, receive the at least one question from the query module, and generate an analysis of the self-reported data, via the one or more machine learning models; and wherein the user device and the provider device include respective message modules, the remote computing unit being configured to provide two-way communication between the eye care provider and the user based in part on the analysis, via the respective message modules in the form of a reply to the at least one question, based in part on the one or more machine learning models.

11. The personalized assistance system of claim 10, wherein:

the remote computing unit includes a first cloud unit and a central server, the controller being embedded in at least one of the first cloud unit and the central server.

12. The personalized assistance system of claim 10, wherein:

the remote computing unit includes a first database storing respective information pertaining to the user, including a type of the vision correction device;

the remote computing unit includes a second database storing group data pertaining to a group of users, the group data at least partially including respective self-reported data of the group of users; and the user device includes a comparative tracking module configured to enable the user to compare the self-reported data with the group data.

13. The personalized assistance system of claim 10, wherein assisting the user based in part on the analysis includes at least one of:

providing coaching on taking care of at least one of the vision correction device and an eye of the user;

suggesting a follow-up visit with an eye care provider; and suggesting an alternative vision correction product.

14. The personalized assistance system of claim 10, wherein:

the vision correction device is a contact lens.

15. The personalized assistance system of claim 14, wherein:

the contact lens is a multi-focal lens having a first zone for distance vision, a second zone for near vision and a third zone for intermediate vision.

16. The personalized assistance system of claim 14, wherein the one or more preselected questions include:

an inquiry into a comfort level of the user, including at least one of a dryness factor and an irritation factor.

17. The personalized assistance system of claim 14, wherein the one or more preselected questions include:

an inquiry into when the user last cleaned the vision correction device.

* * * * *